United States Patent
Ishibuchi et al.

[11] Patent Number: 6,015,829
[45] Date of Patent: Jan. 18, 2000

[54] 1-PHENYLPYRAZOLE COMPOUNDS AND MEDICINAL APPLICATION THEREOF

[75] Inventors: Seigo Ishibuchi; Hiroshi Morimoto; Atsushi Fukunari; Hiroyoshi Inoue; Yoichi Naka, all of Fukuoka, Japan

[73] Assignee: Yoshitomi Pharmaceutical Industries, ltd., Japan

[21] Appl. No.: 09/155,155

[22] PCT Filed: Oct. 22, 1997

[86] PCT No.: PCT/JP97/03840

§ 371 Date: Sep. 22, 1998

§ 102(e) Date: Sep. 22, 1998

[87] PCT Pub. No.: WO98/18765

PCT Pub. Date: May 7, 1998

[30]  Foreign Application Priority Data

| Oct. 25, 1996 | [JP] | Japan | 8-284479 |
| Mar. 11, 1997 | [JP] | Japan | 9-055786 |
| Sep. 26, 1997 | [JP] | Japan | 9-261305 |

[51] Int. Cl.[7] ............ A61K 31/415; C07D 231/14; C07D 231/38
[52] U.S. Cl. ............ 514/404; 514/406; 548/372.5; 548/374.1
[58] Field of Search ............ 548/372.5, 374.1; 514/404

[56] References Cited

U.S. PATENT DOCUMENTS

| 4,346,094 | 8/1982 | Beck et al. |
| 4,472,192 | 9/1984 | Eicken et al. |
| 4,495,195 | 1/1985 | Beck et al. |
| 4,734,122 | 3/1988 | Gehring et al. |
| 4,791,212 | 12/1988 | Gehring et al. |
| 5,064,851 | 11/1991 | Goddard et al. |

FOREIGN PATENT DOCUMENTS

| 0 151 866 | 8/1985 | European Pat. Off. |
| 0 151 867 | 8/1985 | European Pat. Off. |
| 0 177 242 | 4/1986 | European Pat. Off. |
| 0 513 379 | 11/1992 | European Pat. Off. |
| 55-27916 | 7/1980 | Japan |
| 6-211815 | 8/1994 | Japan |

OTHER PUBLICATIONS

*Derwent Abstracts*, Abstract No. 91–242294/33 (abstract of JP 3–157385).

*Primary Examiner*—Robert W. Ramsuer
*Attorney, Agent, or Firm*—Wenderoth, Lind & Ponack, L.L.P.

[57] ABSTRACT

1-Phenylpyrazole compounds of the formula (1):

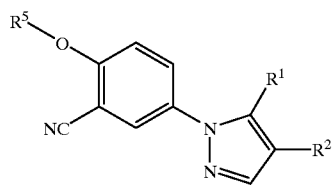

which is exemplified by 5-amino-1-(3-cyano-4-isobutoxyphenyl)pyrazole-4-carboxylic acid, an optical isomer thereof and a pharmaceutically acceptable salt thereof. These compounds have a xanthine oxidase inhibitory activity and are useful as therapeutic agents for diseases such as hyperuricacidemia and gout.

5 Claims, No Drawings

1-PHENYLPYRAZOLE COMPOUNDS AND MEDICINAL APPLICATION THEREOF

TECHNICAL FIELD

The present invention relates to a novel 1-phenylpyrazole compound that has a xanthine oxidase inhibitory activity and that can be used as a therapeutic agent for hyperuricacidemia and gout, as well as a therapeutic agent or preventive agent of various diseases caused by the generation of active oxygen, a pharmaceutical composition comprising the same and a medicament comprising the same.

BACKGROUND ART

There have been published the following patent applications drawn to xanthine oxidase inhibitors. For example, Japanese Patent Unexamined Publication No. 95272/1984 discloses 3-phenylpyrazole derivatives having a xanthine oxidase inhibitory activity, Japanese Patent Unexamined Publication No. 85379/1982 discloses 3-phenylisothiazole derivatives having a xanthine oxidase inhibitory activity, WO92/09279 discloses 2-phenylthiazole derivatives having a xanthine oxidase inhibitory activity, and Japanese Patent Unexamined Publication No. 211815/1994 discloses 3-phenylisoxazole derivatives having xanthine oxidase inhibitory activity. While Japanese Patent No. 2504659 discloses 1-phenylpyrazolecarboxylate that is used as a synthetic intermediate for drugs, it does not disclose its xanthine oxidase inhibitory activity or use as a therapeutic agent of hyperuricacidemia and gout.

The hyperuricacidemia and gout (acute arthritis) resulting therefrom are highly frequently found in middle-aged males. It is said that the numbers of old patients and younger patients are on the rise due to diverse eating habits of these days. A therapeutic agent of hyperuricacidemia includes uricosuric agents and uric acid synthesis inhibitors, and is selected depending on the disease state of hyperuricacidemia. As the uricosuric agent, benzbromarone, probenecid and sulfinpyrazone have been used, while as the uric acid synthesis inhibitor, allopurinol alone has been used. This allopurinol is a stereoisomer of hypoxanthine and inhibits xanthine oxidase. This inhibition leads to the suppression of uric acid production and decrease in blood uric acid level However, allopurinol is known to cause side effects such as hypersensitive symptoms (e.g., anthema, hives and the like) or renal and hepatic disorders. In particular, the hypersensitive symptoms has been reported to be caused by a metabolite of allopurinol, such as oxypurinol [The American Journal of Medicine, vol. 76, p. 47 (1984)]. Thus, it appears that a compound having a structure not analogous to hypoxanthines has a potential of avoiding side effects.

Therefrom it is suggested that a compound having a novel structure not analogous to hypoxanthine and showing xanthine oxidase inhibitory activity will make a therapeutic agent with less side effects for hyperuricacidemia and gout Thus, the present invention aims at providing a therapeutic agent for hyperuricacidemia and gout, which has a strong xanthine oxidase inhibitory activity and a sustained lowering action on uric acid level in blood, and which causes less side effects as compared to conventional compounds.

Meanwhile, generation of active oxygen has been documented to be responsible for many diseases, such as various ischemic perfusion disorders, inflammatory diseases, diabetes, malignant tumor, arteriosclerosis, neuropathy and the like. Therefore, a substance capable of suppressing generation of active oxygen is considered to be effective for the treatment and prophylaxis of these diseases. Inasmuch as xanthine oxidase has been noted as an enzyme involved in the generation of active oxygen, an inhibitor of xanthine oxidase is expected to suppress generation of active oxygen.

Allopurinol which is a xanthine oxidase inhibitor and known as a therapeutic agent of hyperuricacidemia and gout, as well as a xanthine oxidase inhibitor disclosed in Japanese Patent Unexamined Publication No. 157385/1991 have been studied with regard to the inhibitory effect on organopathy caused by the generation of active oxygen due to ischemic perfusion. The studies are inconclusive since some assert that they are effective for animal models with ischemic perfusion disorder and some assert otherwise. Consequently, a practical use of a substance capable of suppressing generation of active oxygen has not been realized at the present stage.

DISCLOSURE OF THE INVENTION

The present inventors have conducted intensive studies in an attempt to develop a therapeutic agent of hyperuricacidemia and gout, or a therapeutic or preventive agent for various organopathy caused by the generation of active oxygen, and have found that 1-phenylpyrazole compound of the following formula (1), an optical isomer thereof and a pharmaceutically acceptable salt thereof have selective and strong inhibitory activity against xanthine oxidase, that they are useful drugs effective for hyperuricacidemia and gout caused thereby, in view of the strong and sustained lowering action on uric acid level in blood as demonstrated by in vivo tests, and that a highly safe therapeutic agent of hyperuricacidemia and gout, which causes less side effects such as hypersensitive symptoms (e.g., anthema, hives and the like) or renal and hepatic disorders, seen when a conventional, hypoxanthine-like therapeutic agent of hyperuricacidemia and gout is administered, which resulted in the completion of the present invention.

Accordingly, the present invention relates to a 1-phenylpyrazole compound of the formula (1)

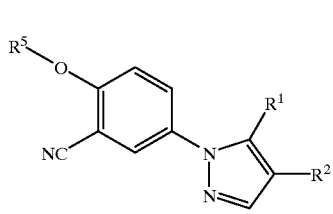

(1)

wherein
$R^1$ is a hydrogen, a halogen or an amino;
$R^2$ is a carboxy or a $C_1$–$C_4$ alkoxycarbonyl; and
$R^5$ is a $C_4$–$C_6$ alkyl, a $C_3$–$C_6$ cycloalkyl or a $C_3$–$C_6$ cycloalkyl-$C_1$–$C_4$ alkyl optionally substituted by 1 or 2 substituents selected from the group consisting of halogen, hydroxy, $C_1$–$C_4$ alkoxy, carboxy, $C_1$–$C_4$ alkoxycarbonyl and acyloxy,
an optical isomer thereof and a pharmaceutically acceptable salt thereof.

The present invention also provides a pharmaceutical composition comprising the 1-phenylpyrazole comound of the formula (1), an optical isomer thereof or a pharmaceutically acceptable salt thereof, and a pharmaceutically acceptable carrier, as well as a medicament and xanthine oxidase inhibitor comprising the 1-phenylpyrazole comound of the formula (1), an optical isomer thereof or a pharmaceutically acceptable salt thereof In the formula (1), halogen at $R^1$ is fluorine, chlorine, bromine or iodine.

The $C_1$–$C_4$ alkoxycarbonyl at $R^2$ is alkoxycarbonyl wherein the alkoxy moiety has 1 to 4 carbon atoms, such as methoxycarbonyl, ethoxycarbonyl, propoxycarbonyl, isopropoxycarbonyl, butoxycarbonyl, isobutoxycarbonyl, tert-butoxycarbonyl and the like.

The $C_4$–$C_6$ alkyl at $R^5$ is a linear or branched alkyl having 4 to 6 carbon atoms, such as 2-ethylpropyl, butyl, isobutyl, sec-butyl, tert-butyl, pentyl, 1-methylbutyl, 2-methylbutyl, 3-methylbutyl, neopentyl, hexyl, 2-ethylbutyl and the like. The $C_3$–$C_6$ cycloalkyl is cycloalkyl having 3 to 6 carbon atoms and is exemplified by cyclopropyl, cyclopentyl, cyclohexyl and the like. The $C_3$–$C_6$ cycloalkyl moiety of $C_3$–$C_6$ cycloalkyl-$C_1$–$C_4$ alkyl is exemplified by those exemplified above, and the $C_1$–$C_4$ alkyl moiety thereof may be linear or branched alkyl having 1 to 4 carbon atoms, which is exemplified by methyl, ethylpropyl, butyl, isobutyl, sec-butyl, tert-butyl and the like. Examples of $C_3$–$C_6$ cycloalkyl-$C_1$–$C_4$ alkyl include cyclopropylmethyl, cyclopentylmethyl, cyclohexylmethyl, 2-cyclohexylethyl, 3-cyclohexylpropyl,4-cyclohexylbutyl and the like.

Examples of halogen which is a substituent optionally substituting $R^5$ include fluorine, chlorine, bromine and iodine. The $C_1$–$C_4$ alkoxy is alkoxy having 1 to 4 carbon atoms, such as methoxy, ethoxy, propoxy, isopropoxy, butoxy, isobutoxy, sec-butoxy, tert-butoxy and the like. The $C_1$–$C_4$ alkoxycarbonyl is alkoxycarbonyl wherein the alkoxy moiety has 1 to 4 carbon atoms, such as methoxycarbonyl, ethoxycarbonyl, propoxycarbonyl, isopropoxycarbonyl, butoxycarbonyl, isobutoxycarbonyl, tert-butoxycarbonyl and the like. Examples of acyloxy include acetoxy, propionyloxy, butyrloxy, isobutyryloxy, valeryloxy, isovaleryloxy, hexanoyloxy, octanoyloxy, benzoyloxy and the like.

The $C_4$–$C_6$ alkyl optionally substituted by 1 or 2 substituents selected from halogen, hydroxy, $C_1$–$C_4$ alkoxy, carboxy, $C_1$–$C_4$ alkoxycarbonyl and acyloxy is exemplified by 3-fluoro-3-fluoromethylpropyl, 3-fluoro-2,2-dimethylpropyl, 2,2-dimethyl-3-hydroxypropyl, 2,2-dimethyl-3-methoxypropyl, 2-carboxy-2-methylpropyl, 3-acetyloxy-2,2-dimethylpropyl, 3-benzoyloxy-2,2-dimethylpropyl and the like.

As $R^1$, hydrogen is particularly preferable. As $R^2$, carboxy is particularly preferable. As $R^5$, $C_4$–$C_6$ alkyl is particularly preferable.

Preferable compounds of the formula (1) are the following.

(2) 5-amino-1-(3-cyano-4-isobutoxyphenyl)pyrazole-4-carboxylic acid, (3) ethyl 1-(3-cyano-4-isobutoxyphenyl)pyrazole4-carboxylate, (4) 1-(3-cyano-4-isobutoxyphenyl)pyrazole carboxylic acid, (8) 1-(4-butoxy-3-cyanophenyl)pyrazole-4-carboxylic acid,

(10) 1-(3-cyano-4-cyclopropylmethoxyphenyl)pyrazole-4-carboxylic acid,

(12) 1-(3-cyano-4-neopentyloxyphenyl)pyrazole-4-carboxylic acid,

(14) 1-(3-cyano-4-(2-ethylbutoxy)phenyl)pyrazole-4-carboxylic acid,

(16) 1-(3-cyano-4-(1-ethylpropoxy)phenyl)pyrazole-4-carboxylic acid,

(18) 1-(3-cyano-4-(3-methylbutoxy)phenyl)pyrazole-4-carboxylic acid,

(28) 1-(3-cyano-4-((S)-2-methylbutoxy)phenyl)pyrazole-4-carboxylic acid,

(32) 5-amino-1-(3-cyano-4-neopentyloxyphenyl)pyrazole-4-carboxylic acid, and

(36) 5-chloro-1-(3-cyano-4-neopentyloxyphenyl)pyrazole-4-carboxylic acid, an optical isomer thereof and a pharmaceutically acceptable salt thereof, wherein the numbers refer to Example numbers.

The pharmaceutically acceptable salt of the compound of the formula (1) may be, for example, salts with metal (e.g., sodium, potassium, calcium, lithium, magnesium, aluminum, zinc and the like) at carboxy and salts with organic base (e.g., diethanolamine, ethylenediamine and the like).

The compound of the formula (1) and pharmaceutically acceptable salts thereof may exist as hydrates or solvates. The hydrates thereof (e.g., ½ hydrate, monohydrate, dihydrate and the like) as well as solvates thereof are encompassed in the present invention. When the compound of formula (1) has an asymmetric carbon, at least two kinds of optical isomers are present These optical isomers and racemates thereof are also encompassed in the present invention.

The compound of formula (1) and the compounds within the scope of the formula (1) can be synthesized by the methods shown in the following. Each symbol used in the following reaction formulas are as defined above, unless otherwise specified.

Method (1)

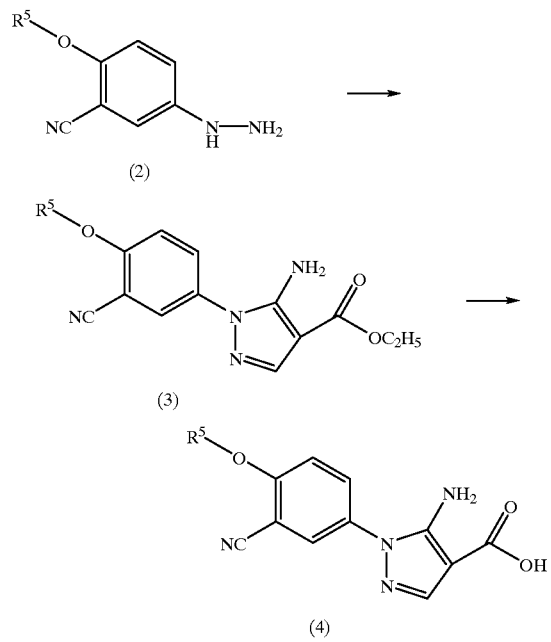

A compound of formula (2) is reacted with ethyl 2-cyano-3-ethoxyacrylate in a suitable solvent (e.g., methanol, ethanol, butanol, ethylene glycol and mixed solvents thereon at a refluxing temperature of the solvent for 1 to 24 hours to give compound of formula (3). This compound is reacted with an alkali (e.g., sodium hydroxide, potassium hydroxide, barium hydroxide, potassium carbonate and the like) or an acid (e.g., hydrochloric acid, sulfuric acid, acetic acid and the like) in a suitable solvent (e.g., ethanol, tetrahydrofuran, water, acetone, dimethylformamide and mixed solvents thereof at room temperature or at a refluxing temperature of the solvent for 1 to 24 hours to give compound of formula (4).

Method (2)

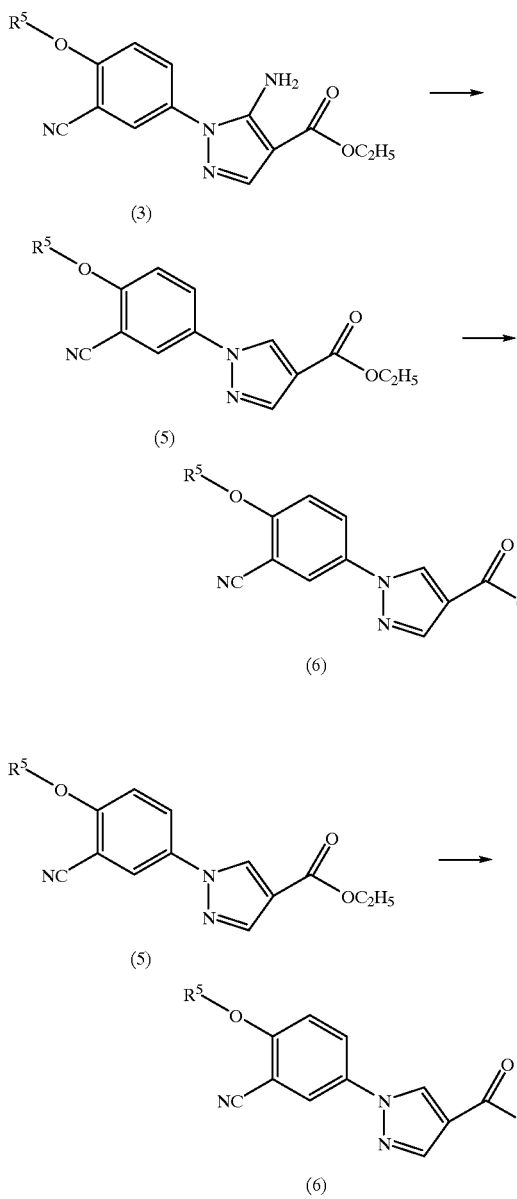

Method (3)

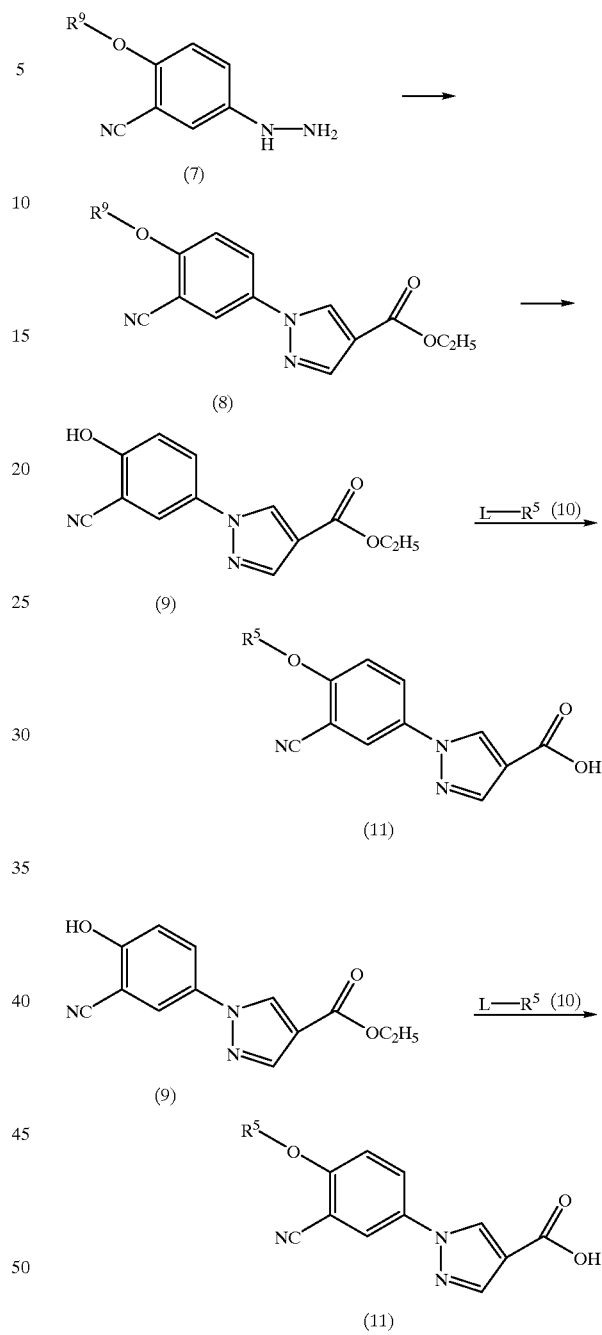

A compound of formula (3) is reacted with hydroxylamine-O-sulfonic acid in an aqueous solution of alkali (e.g., sodium hydroxide, potassium hydroxide and the like) under ice-cooling or at room temperature for 1 to 24 hours, or its diazonium salt obtained by reacting a nitrite by a conventional method is reacted with hypophosphorous acid under ice-cooling or at room temperature for 1 to 24 hours, or it is reacted with isoamyl nitrite in a suitable solvent (e.g., tetrahydrofuran, methanol, ethanol, butanol, ethylene glycol and mixed solvents thereon at a refluxing temperature of the solvent for 1 to 24 hours to give compound of formula (5). This compound is reacted with an alkali (e.g., sodium hydroxide, potassium hydroxide, barium hydroxide, potassium carbonate and the like) or an acid (e.g., hydrochloric acid, sulfuric acid, acetic acid and the like) in a suitable solvent (e.g., ethanol, tetrahydrofuran, water, acetone, dimethylformamide and mixed solvents thereof at room temperature or at a refluxing temperature of the solvent for 1 to 24 hours to give compound of formula (6).

A compound of formula (7) wherein $R^9$ is a protecting group which does not interfere with the reaction, such as methyl and benzyl, is reacted with ethyl 2-cyano-3-ethoxyacrylate in a suitable solvent (e.g., methanol, ethanol, butanol, ethylene glycol and mixed solvents thereof at a refluxing temperature of the solvent for 1 to 24 hours to give compound. This compound is reacted with hydroxylamine-O-sulfonic acid in an aqueous solution of alkali (e.g., sodium hydroxide, potassium hydroxide and the like) under ice-cooling or at room temperature for 1 to 24 hours, or with isoamyl nitrite in a suitable solvent (e.g., tetrahydrofuran, methanol, ethanol, butanol, ethylene glycol and mixed solvents thereof) at a refluxing temperature of the solvent for 1 to 24 hours to give compound of formula (8). This compound is deprotected by catalytic hydrogenation or by the use of a Lewis add (e.g., aluminum chloride) to give compound of formula (9). Tis compound is reacted with comound of formula (10) wherein L is chlorine, bromine, iodine, methanesulfonyloxy, p-toluenesulfonyloxy, trifluoromethanesulfonyloxy and the like, in a suitable solvent which does not adversely influence the reaction (e.g., tetrahydrofuran, dichloromethane, dimethylformamide and mixed solvents thereof in the presence of a base (e.g., potassium carbonate, sodium hydroxide, triethylamine, pyridine, dimethylaminopyridine and the like) at room temperature or at a refluxing temperature of the solvent for 1 to 24 hours, and then with a base (e.g., sodium hydroxide, potassium hydroxide, barium hydroxide, potassium carbonate and the like) or an acid (e.g., hydrochloric acid, sulfuric acid, acetic acid and the like) in a suitable solvent (e.g., ethanol, tetrahydrofuran, water, acetone, dimethylformamide and mixed solvents thereon at room temperature or at a refluxing temperature of the solvent for 1 to 24 hours to give compound of formula (11).

Method (4)

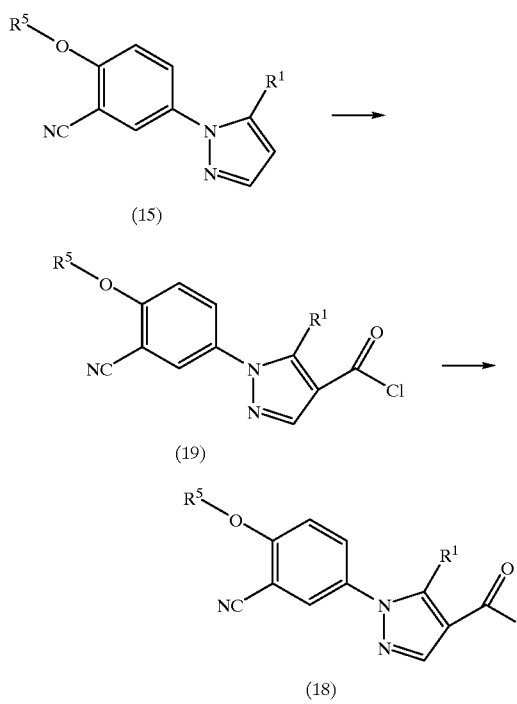

A comound of formula (15) and oxalyl chloride are reacted at room temperature or at a refluxing temperature for 1 to 24 hours to give compound of formula (19). This comound is added to ice water and reacted for 1 to 24 hours to give compound of formula (18)

Method (5)

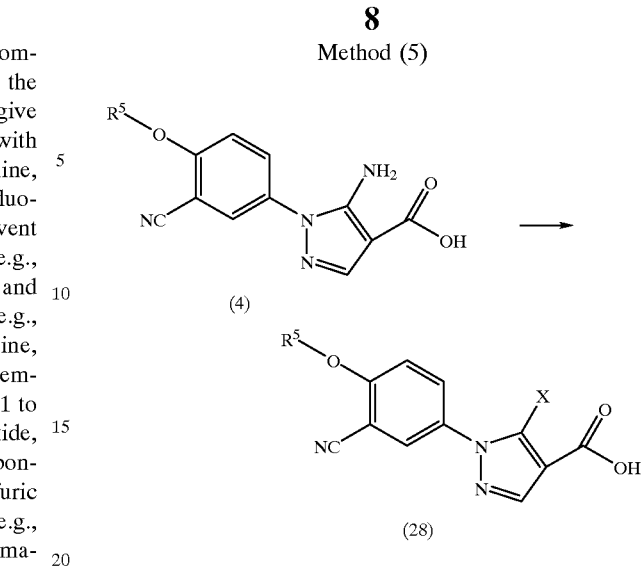

According to a conventional method, an aqueous solution of compound of formula (4) is reacted with a nitrite in the presence of an acid (e.g., hydrochloric acid, hydrobromic acid and hydroiodic acid) to give a solution of the corresponding diazonium salt. The aqueous solution of this compound is reacted with cuprous chloride solution, cuprous bromide solution, potassium iodide or sodium fluoroborate under ice-cooling or under heating for 1 to 24 hours to give compound of formula (28) wherein X is chlorine atom, bromine atom, iodine atom or fluorine atom.

Method (6)

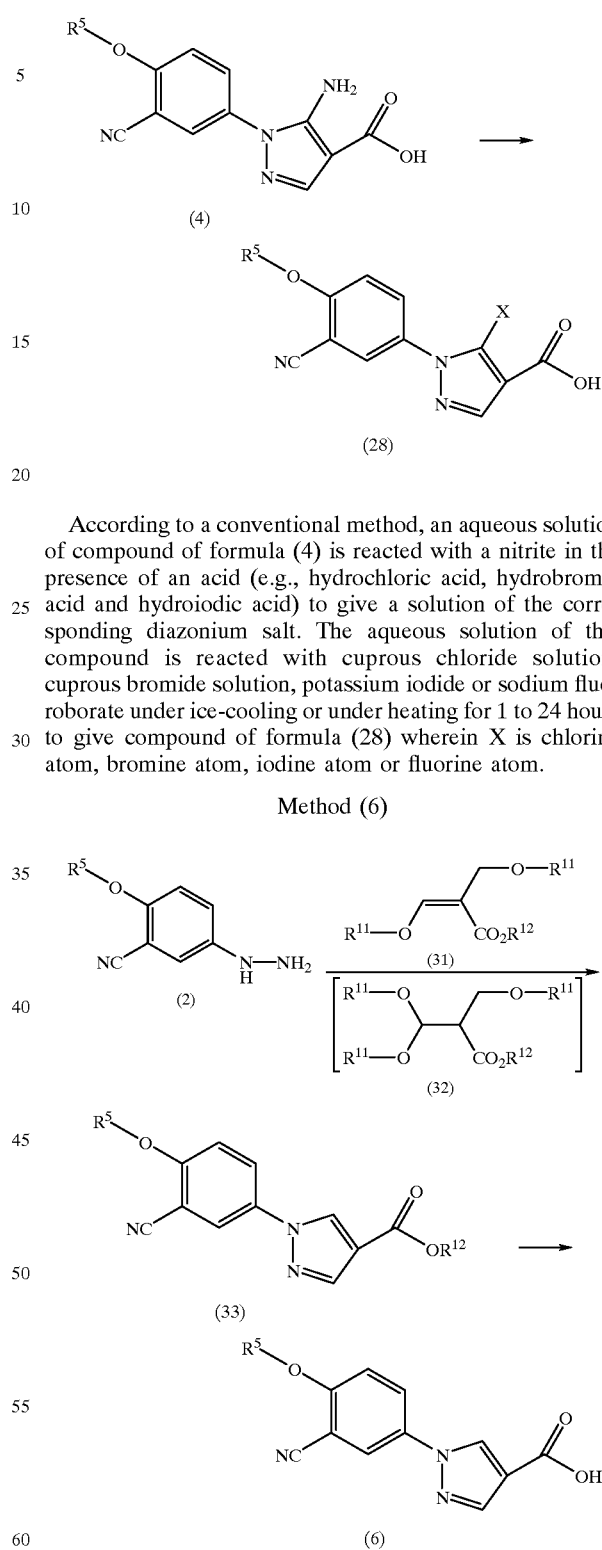

A compound of formula (2) is reacted with compound of formula (31) or (32) wherein $R^{11}$ is alkyl or aralkyl, and $R^{12}$ is hydrogen, alkyl or aralkyl in a suitable solvent (e.g., methanol, ethanol, butanol, ethylene glycol and mixed solvents thereof) in the presence of a catalytic amount of an acid at a refluxing temperature of the solvent for 1 to 24 hours to give compound of formula (33). This compound is reacted with an alkali (e.g., sodium hydroxide, potassium hydroxide, barium hydroxide, potassium carbonate and the like) or an acid (e.g., hydrochloric acid, sulfuric acid, acetic acid and the like) in a suitable solvent (e.g., ethanol, tetrahydrofuran, water, acetone, dimethylformamide and mixed solvents thereof) at room temperature or at a refluxing temperature of the solvent for 1 to 24 hours to give compound of formula (6).

Method (7)

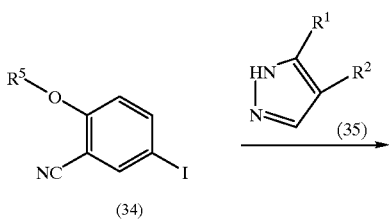

(34)

(1)

A compound of formula (34) is reacted with compound of formula (35) in a suitable solvent (e.g., benzene, toluene, tetrahydrofuran, dichloromethane, dimethylformamide and mixed solvents thereof) in the presence of potassium fluoride and copper powder and a base (e.g., potassium carbonate, sodium carbonate, potassium hydroxide and the like) at a refluxing temperature of the solvent for 1 to 24 hours to give compound of formula (1).

Method (8)

A compound of formula (18) is reacted with compound of formula (40)

 (40)

wherein $R^{13}$ is $C_1$–$C_4$ alkyl in a suitable solvent (e.g., tetrahydrofuran, dichloromethane, dimethylformamide and mixed solvents thereof which does not interfere with the reaction, in the presence of a tertiary amine such as triethylamine and a condensing agent (e.g., 1,3-dicyclohexylcarbodiimide, 1-ethyl-3-(3-dimethylaminopropyl) carbodiimide, cyanophosphonic diester and the like) under ice-cooling or at room temperature for 1 to 24 hours to give compound of formula (41)

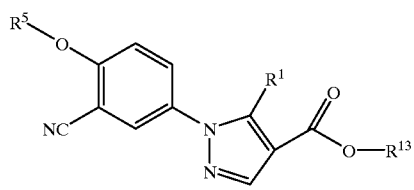

(41)

wherein each symbol is as defined above. When a reactive derivative (e.g., acid chloride, acylimidazole and the like) of compound of formula (18) is used, the reaction proceeds in a suitable solvent (e.g., tetrahydrofuran, dichloromethane, chloroform, benzene and mixed solvents thereof) which does not interfere with the reaction, in the presence of a tertiary amine such as triethylamine or pyridine under ice-cooling or at room temperature for 1 to 24 hours.

Method (9)

A compound of formula (18) is reacted with compound of formula (42)

$$R^{13}\text{—L} \qquad (42)$$

wherein $R^{13}$ and L are as defined above, in a suitable solvent (e.g., tetrahydrofuran, dichloromethane, benzene, dimethylformamide and mixed solvents thereof) which does not interfere with the reaction, in the presence of a base such as triethylamine, pyridine, potassium carbonate and the like under ice-cooling or under heating for 1 to 24 hours to give compound of formula (41).

Method (10)

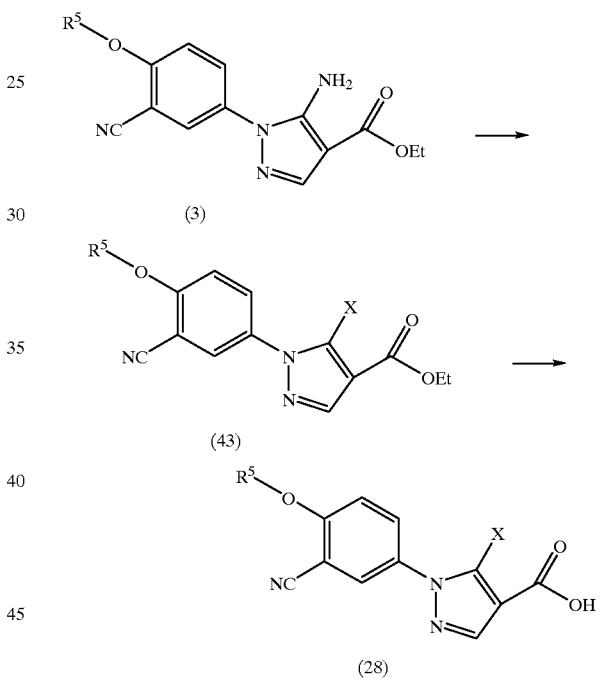

An aqueous solution of compound of formula (3) is reacted with a nitrite by a conventional method in the presence of an acid (e.g., hydrochloric acid, hydrobromic acid, hydroiodic acid and the like) to give a solution of the corresponding diazonium salt The aqueous solution of is compound is reacted with cuprous chloride solution, cuprous bromide solution, potassium iodide or sodium fluoroborate under ice-cooling or under heating for 1 to 24 hours to give compound of formula (43). This compound is reacted with an alkali (e.g., sodium hydroxide, potassium hydroxide, barium hydroxide, potassium carbonate and the like) or an acid (e.g., hydrochloric acid, sulfuric acid, acetic acid and the like) in a suitable solvent (e.g., ethanol, tetrahydrofuran, water, acetone, dimethylformamide and mixed solvents thereon at room temperature or at a refluxing temperature of the solvent for 1 to 24 hours to give compound of formula (28) wherein X is a chlorine atom, bromine atom, iodine atom or fluorine atom.

Method (11)

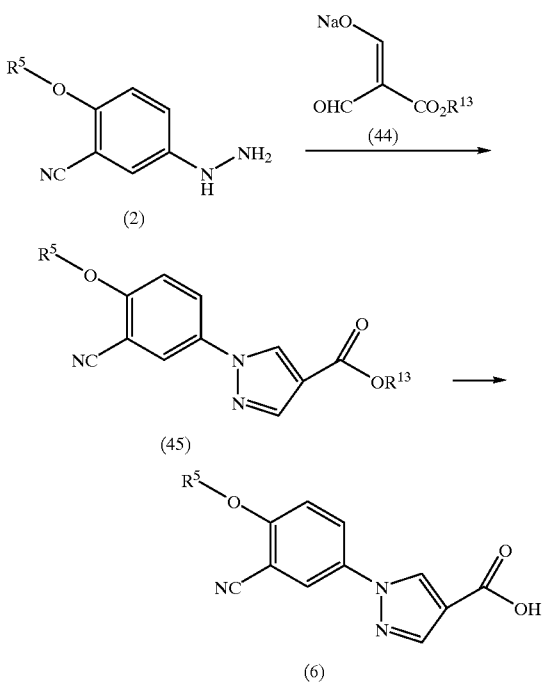

A compound of formula (2) is reacted with compound of formula (44) wherein $R^{13}$ is as defined above which is obtained by a method described in J. Am. Chem. Soc., 75, 4048 (1953) in a suitable solvent (e.g., diethyl ether, tetrahydrofuran, toluene, water and mixed solvents thereof in the presence of an acid (e.g., acetic acid, hydrochloric acid, sulfuric acid and the like) at room temperature or a refluxing temperature of the solvent for 1 to 24 hours to give compound of formula (45). This compound is reacted with an alkali (e.g., sodium hydroxide, potassium hydroxide, barium hydroxide, potassium carbonate and the like) or an acid (e.g., hydrochloric acid, sulfuric acid, acetic acid and the like) in a suitable solvent (e.g., ethanol, tetrahydrofuran, water, acetone, dimethylformamide and mixed solvents thereof) at room temperature or at a refluxing temperature of the solvent for 1 to 24 hours to give compound of formula (6).

The compound of formula (1) can be converted to a salt by a treatment with metal hydroxide (e.g., sodium hydroxide, potassium hydroxide, calcium hydroxide, lithium hydroxide, magnesium hydroxide, aluminum hydroxide, zinc hydroxide and the like), alkali metal carbonate or hydrogencarbonate (e.g., sodium carbonate, sodium hydrogencarbonate, potassium hydrogencarbonate and the like), or organic base (e.g., diethanolamine, ethylenediamine and the like).

The compound of the present invention thus obtained can be isolated and purified by a conventional method such as recrystallization and column chromatography. When the product thus obtained is a racemate, it can be resolved into a desired optically active compound by preparative recrystallization using a salt with optically active acid or base, or by passing through a column packed with an optically active carrier. Respective diastereomers can be separated by a method such as preparative crystallization and column chromatography. These can be also obtained by the use of an optically active starting compound. Stereoisomers can be isolated by recrystallization and column chromatography.

The 1-phenylpyrazole compound of the present invention, an optical isomer thereof and a pharmaceutically acceptable salt thereof are xanthine oxidase inhibitors having a selective and strong inhibitory activity against xanthine oxidase. In view of the strong and long-lasting blood uric acid value-lowering action in vivo tests, they can make useful medicaments effective for hyperuricacidemia and gout resulting therefrom. In addition, they are expected to make highly safe therapeutic agents of hyperuricacidemia and gout, which cause less side effects such as hypersensitive symptoms (e.g., anthema, hives and the like) or renal and hepatic disorders, which are seen when a conventional, hypoxanthine-like therapeutic drug of hyperuricacidemia and gout is administered. The compound of the present invention is expected to be usable as a therapeutic agent of diseases such as hyperuricacidemia, gout and the like, which shows long duration of effects by a single administration a day. The compound of the present invention is used for the treatment and prevention of diseases caused by various disorders associated with the generation of active oxygen in organs and tissues. For example, it can be used for diseases associated with ischemic perfusion disorder in various organs, which is caused by the generation of active oxygen. Specific examples include myocardial infarction, cerebral infarction, pulmonary thrombosis, renal and hepatic ischemic organopathy, and postoperative or post-treatment aggravation of the state associated with transdermal and transcervical coronary arterioplasty, vascular bypassing or organ transplantation, which have high possibility of developing temporal ischemic state.

When the compound of the present invention is used as a medicament, the compound of the present invention is admixed with a carrier acceptable in pharmaceutical formulation (e.g., excipients, binders, disintegrators, correctives, corrigents, emulsifiers and the like), diluents, solubilizers and the like to give a pharmaceutical composition. This composition is prepared by a conventional method into tablets, capsules, granules, powders, syrups, suspensions, solutions, injections, transfusions or suppositories, which may be administered orally or parenterally.

When tablets are used for oral administration, sucrose, lactose, mannitol, maltitol, dextran, corn starch and the like are generally used as a carrier, and generally, lubricants such as magnesium stearate, preservatives such as p-hydroxybenzoates, sorbic acid and salts thereof, and the like, antioxidants such as ascorbic acid, α-tocopherol, cystine and the like, disintegrators, binders and the like are added. Tablets may be enteric-coated. When capsules are used for oral administration, effective diluents are lactose and dry corn starch. Liquid agents for oral use are exemplified by syrups, suspensions, solutions and the like, which may contain an inert diluent generally used in this field, such as water. These may contain sweeteners and/or flavors.

In the case of parenteral administration such as subcutaneous injection, intravenous injection, intramuscular injection, intraperitoneal injection and transfusion, it is a general practice to prepare a sterile solution containing an active ingredient, adjust the pH of the solution and buffersize the solution. Vehicle usable for this end and those acceptable as a solvent include water, Ringer solution, isotonic brine and the like. When in use for intravenous injection, the total concentration of the solute is adjusted to make the solution thereof isotonic.

Suppositories can be produced by admixing a drug with a suitable nonirritant excipient, such as cocoa butter and polyethylene glycols, which is solid at normal temperature and liquid at temperature in intestines and melted in rectum to release a drug.

The dose is determined in consideration of age, body weight, administration time, administration route, combination with other drugs, disease state of patients undergoing the treatment and other factors. The compound of the present invention, an optical isomer thereof and a pharmaceutically acceptable salt thereof are low toxic and can be used safely. The daily dose varies depending on conditions and body weight of patients, the kind of compound, administration route and the like. It is about 0.01–150 mg/patient/day, preferably 0.1–100 mg/patient/day, for oral administration, and about 0.01–50 mg/patient/day, preferably 0.01–20 mg/patient/day, for parenteral administration by a subcutaneous, intravenous, intramuscular or intrarectum route.

The present invention is explained in more detail by way of Starting Material Synthetic Examples, Examples, Formulation Examples and Experimental Examples, to which the present invention is not limited.

STARTING MATERIAL SYNTHETIC EXAMPLE 1

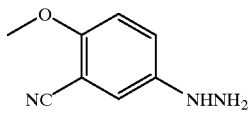

To an aqueous solution (150 ml) of 3-cyano-4-methoxyaniline hydrochloride (72 g) were added sodium nitrite (29.7 g), stannous chloride dihydrate (266 g) and con. hydrochloric acid (437 ml) with stirring under ice-cooling. After the completion of the reaction, precipitated crystals were collected by filtration. The crystals were added to water, and the mixture was neutralized with aqueous sodium hydroxide solution, extracted with a mixed solvent of toluene and tert-butanol, washed with water and dried over magnesium sulfate. The solvent was evaporated under reduced pressure to give 44 g of 3-cyano-4-methoxyphenylhydrazine.

STARTING MATERIAL SYNTHETIC EXAMPLE 2

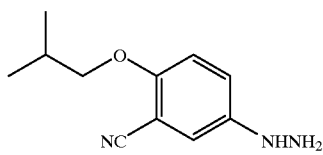

To an aqueous solution (34 ml) of 3-cyano-4-isobutoxyaniline hydrochloride (20 g) were added sodium nitrite (6.8 g), stannous chloride dihydrate (61 g) and con. hydrochloric add (100 ml) with stirring under ice-cooling. After the completion of the reaction, precipitated crystals were collected by filtration. The crystals were added to water, and the mixture was neutralized with aqueous sodium hydroxide solution, extracted with a mixed solvent of toluene and tert-butanol, washed with water and dried over magnesium sulfate. The solvent was evaporated under reduced pressure to give 15 g of 3-cyano-4-isobutoxy-phenylhydrazine.

STARTING MATERIAL SYNTHETIC EXAMPLE 3

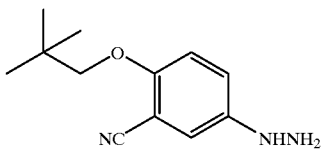

To an aqueous solution (33 ml) of 3-cyano-4-neopentyloxyaniline hydrochloride (21 g) were added sodium nitrite (6.7 g), stannous chloride dihydrate (59.5 g) and con. hydrochloric add (100 ml) with stirring under ice-cooling. After the completion of the reaction, precipitated crystals were collected by filtration The crystals were added to water, and the mixture was neutralized with aqueous sodium hydroxide solution, extracted with a mixed solvent of toluene and tert-butanol, washed with water and dried over magnesium sulfate. The solvent was evaporated under reduced pressure to give 17 g of 3-cyano-4-neopentyloxy-phenylhydrazine.

STARTING MATERIAL SYNTHETIC EXAMPLE 4

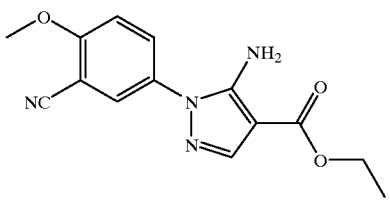

To a solution (300 ml) of 3-cyano-4-methoxyphenyl hydrazine (44 g) obtained in Starting Material Synthetic Example 1 in ethanol was added ethyl 2-cyano-3-ethoxyacrylate (45 g) with stirring, and the mixture was refluxed under heating for 2 hours. After the completion of the reaction, the reaction mixture was cooled and the precipitated crystals were recrystallized from dichloroethane to give 67.2 g of ethyl 5-amino-1-(3-cyano-4-methoxyphenyl) pyrazole-4-carboxylate, melting point 195–196° C.

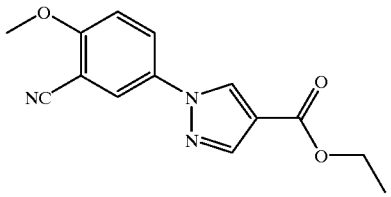

Then, to a solution (286 ml) of ethyl 5-amino-1-(3-cyano-4-methoxyphenyl) pyrazole-4-carboxylate (28.6 g) in tetrahydrofuran was added isoamyl nitrite (35 g) with stirring, and the mixture was refluxed under heating for 7 hours. After the completion of the reaction, the reaction mixture was cooled and the precipitated crystals were collected by filtration to give 24 g of ethyl 1-(3-cyano-4-methoxyphenyl) pyrazole-4-carboxylate, melting point 192–193° C.

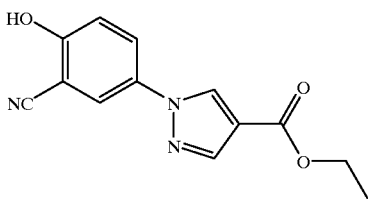

To a solution (280 ml) of ethyl 1-(3-cyano-4-methoxyphenyl)pyrazole-4-carboxylate (28 g) in dichloroethane was added aluminum chloride (47.6 g with stirring, and the mixture was heated at 70° C. for 4 hours. After the completion of the reaction, the reaction mixture was poured into water, extracted with ethyl acetate, washed with water and dried over magnesium sulfate. The solvent was evaporated under reduced pressure and the obtained residue was recrystallized from ethyl acetate to give 22.5 g of ethyl 1-(3-cyano-4-hydroxyphenyl)pyrazole-4-carboxylate, melting point 233–234° C.

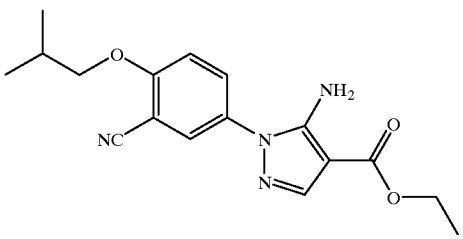

To a solution (50 ml) of 3-cyano-4-isobutoxyphenylhydrazine (5 g) obtained in Starting Material Synthetic Example 2 in ethanol was added ethyl 2-cyano-3-ethocyacrylate (4.2 g) with stirring, and the mixture was refluxed under heating for 2 hours. After cooing, the precipitated crystals were collected by filtration to give 5.1 g of ethyl 5-amino)-1-(3-cyano-4-isobutoxyphenyl)pyrazole-4-carboxylate, melting point 115–171° C.

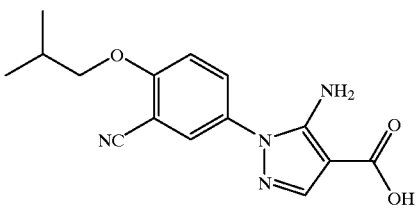

To a solution (10 ml) of ethyl 5-amino-1-(3-cyano-4-isobutoxyphenyl)-pyrazole-4-carboxylate (1 g) in ethanol was added 5 N aqueous sodium hydroxide solution (1 ml) with string, and the mixture was refluxed under heating for 2 hours. After the completion of the reaction, the reaction mixture was poured into water, and the mixture was neutralized with acetic acid. The precipitated crystals were recrystallized from a mixed solvent of dioxane and water to give 0.4 g of 5-amino-1-(3-cyano-4-isobutoxyphenyl) pyrazole-4-carboxylic acid, melting point 204° C. (decomposition).

EXAMPLE 3

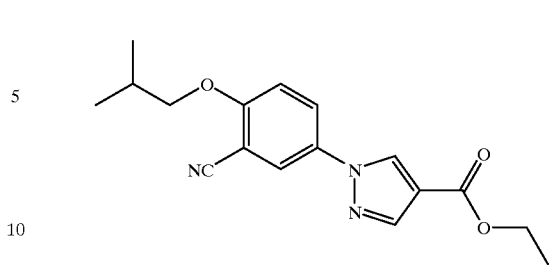

Then, to a solution (16 ml) of ethyl 5-amino-1-(3-cyano-4-isobutoxyphenyl)pyrazole-4-carboxylate (1.64 g) obtained in Example 1 in tetrahydrofuran was added isoamyl nitrite (1.75 g) with stirring, and the mixture was refluxed under heating for 1.5 hours. After the completion of the reaction, the solvent was evaporated under reduced pressure and the obtained residue was recrystallized from ethyl alcohol to give 1.38 g of ethyl 1-(3-cyano-4-isobutoxyphenyl)pyrazole-4-carboxylate, melting point 138–139° C.

EXAMPLE 4

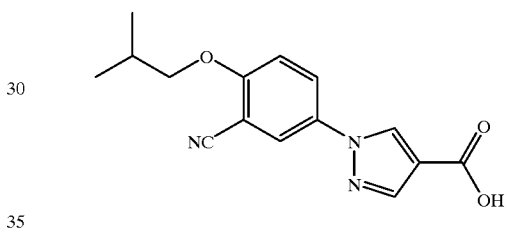

To a solution (15 ml) of ethyl 1-(3-cyano-4-isobutoxyphenyl)pyrazole-4-carboxylate (1.38 g) in ethanol was added 1.75 N aqueous sodium hydroxide solution (3 ml) with stirring, and the mixture was heated at 80° C. for 30 minutes. After the completion of the reaction, the reaction mixture was poured into water and neutralized with acetic acid. The precipitated crystals were recrystallized from a mixed solvent of dioxane and water to give 0.7 g of 1-(3-cyano-4-isobutoxyphenyl)pyrazole-4-carboxylic acid, melting point 192–194° C.

EXAMPLE 5

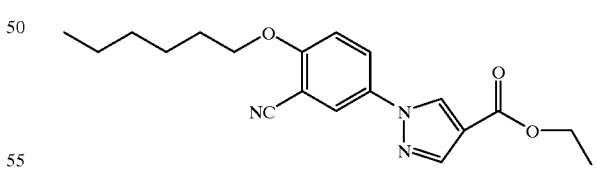

To a solution (10 ml) of ethyl 1-(3-cyano-4-hydroxyphenyl)pyrazole-4-carboxylate (1.5 g) obtained in Starting Material Synthetic Example 4 in dimethylformamide were added potassium carbonate (1.2 g) and hexyl bromide (1.25 g) with stirring, and the mixture was heated at 100° C. for 1 hour. After the completion of the reaction, the reaction mixture was poured into water, extracted with toluene, washed with water and dried over magnesium sulfate. The solvent was evaporated under reduced pressure and the obtained residue was recrystallized from isopropyl ether to give 1.8 g of ethyl 1-(3-cyano-4-hexyloxyphenyl) pyrazole-4-carboxylate, melting point 93–94° C.

EXAMPLE 6

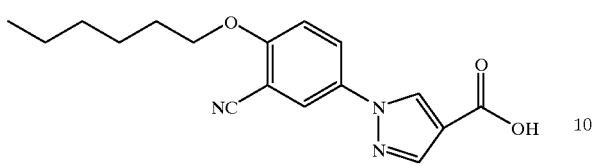

To a solution (20 ml) of ethyl 1-(3-cyano-4-hexyloxyphenyl)pyrazole-4-carboxylate (1.8 g) in ethanol was added 1 N aqueous sodium hydroxide solution (6 ml) with stirring, and the mixture was heated at 50° C. for 1 hour. After the completion of the reaction, the reaction mixture was poured into water and the mixture was neutralized with acetic acid. The precipitated crystals were recrystallized from a mixed solution of dioxane and water to give 1.2 g of 1-(3-cyano-4-hexyloxyphenyl)pyrazole-4-carboxylic acid, melting point 164–165° C.

EXAMPLE 7

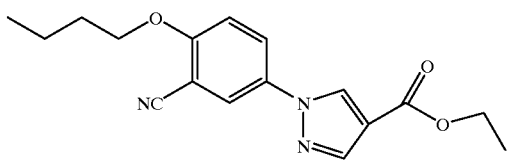

To a solution (10 ml) of ethyl 1-(3-cyano-4-hydroxyphenyl)pyrazole-4-carboxylate (1.5 g) obtained in Sting Material Synthetic Example 4 in dimethylformamide were added potassium carbonate (1.2 g) and butyl bromide (1.04 g) with stirring, and the mixture was heated at 100° C. for 1 hour. After the completion of the reaction, the reaction mixture was poured into water and the precipitated crystals were recrystallized from ethyl alcohol to give 1.5 g of ethyl 1-(4-butoxy-3-cyanophenyl)pyrazole-4-carboxylate, melting point 132° C.

EXAMPLE 8

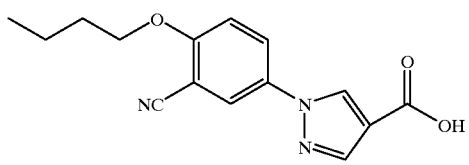

To a solution (15 ml) of ethyl 1-(4-butoxy-3-cyanophenyl)pyrazole-4-carboxylate (1.5 g) in ethanol was added 1.5 N aqueous sodium hydroxide solution (4 ml) with stirring, and the mixture was heated at 80° C. for 1 hour. After the completion of the reaction, the reaction mixture was poured into water and the mixture was neutralized with acetic acid. The precipitated crystals were recrystallized from ethyl acetate to give 0.75 g of 1-(4-butoxy-3-cyanophenyl)pyrazole-4-carboxylic acid, melting point 200–202° C.

EXAMPLE 9

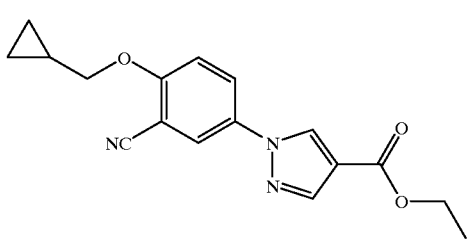

To a solution (10 ml) of ethyl 1-(3-cyano-4-hydroxyphenyl)pyrazole-4-carboxylate (1.5 g) obtained in Starting Material Synthetic Example 4 in dimethylformamide were added potassium carbonate (1.2 g) and cyclopropyhmethyl bromide (1.03 g) with stirring, and the mixture was heated at 100° C. for 1 hour. After the completion of the reaction, the reaction mixture was poured into water and the precipitated crystals were recrystallized from ethyl alcohol to give 1.6 g of ethyl 1-(3-cyano-4-cyclopropylmethoxyphenyl)pyrazole-4-carboxylate, melting point 147–149° C.

EXAMPLE 10

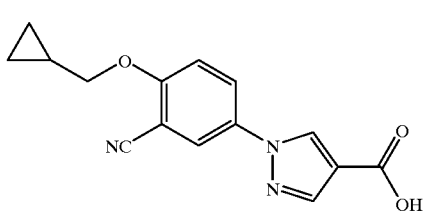

To a solution (15 ml) of ethyl 1-(3-cyano-4-cyclopropylmethoxyphenyl)-pyrazole-4-carboxylate (1.6 g) in ethanol was added 1.5 N aqueous sodium hydroxide solution (4 ml) with stirring, and the mixture was heated at 80° C. for 1 hour. After the completion of the reaction, the reaction mixture was poured into water and the mixture was neutralized with acetic acid. The precipitated crystals were recrystallized from ethyl acetate to give 0.7 g of 1-(3-cyano-4-cyclopropyl-methoxyphenyl)pyrazole-4-carboxylic acid, melting point 210–211° C.

EXAMPLE 11

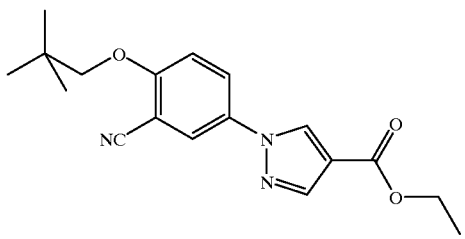

To a solution (50 ml) of ethyl 5-amino-1-(3-cyano-4-neopentyloxyphenyl)-pyrazole-4-carboxylate (5 g) obtained in Example 33 in tetrahydrofuran was added isoamyl nitrite (5.1 g) with stirring, and the mixture was refluxed under heating for 2 hours. After the completion of the reaction, the solvent was evaporated and the obtained residue was recrystallized from ethyl alcohol to give 4.4 g of ethyl 1-(3-cyano-4-neopentyloxyphenyl) pyrazole-4-carboxylate, melting point 154–155° C.

EXAMPLE 12

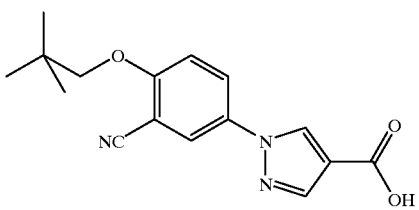

To a solution (20 ml) of ethyl 1-(3-cyano-4-neopentyloxyphenyl)pyrazole4-carboxylate (2 g) in ethanol was added 2 N aqueous sodium hydroxide solution (3.7 ml) with stirring, and the mixture was heated at 80° C. for 30 minutes. After the completion of the reaction, the reaction mixture was poured into water and neutralized with acetic acid. The precipitated crystals were recrystallized from a mixed solution of ethyl alcohol and water to give 0.7 g of 1-(3-cyano-4-neopentyloxyphenyl) pyrazole-4-carboxylic acid, melting point 199–200° C.

EXAMPLE 13

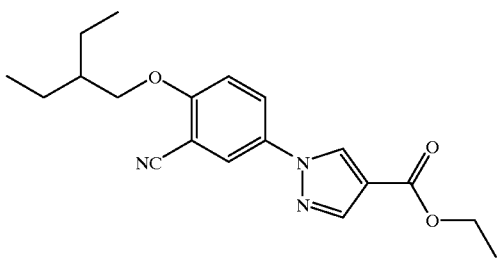

To a solution (10 ml) of ethyl 1-(3-cyano-4-hydroxyphenyl)pyrazole-4-carboxylate (1.5 g) obtained in Staring Material Synthetic Example 4 in dimethylformamide were added potassium carbonate (1.2 g) and 1-chloro-2-ethylbutane (1.4 g) with stirring, and the mixture was heated at 100° C. for 2 hours. After the completion of the reaction, the reaction mixture was poured into water and the mixture was extracted with toluene, washed with water and dried over magnesium sulfate. The solvent was evaporated under reduced pressure, and the obtained residue was recrystallized from isopropyl ether to give 0.88 g of ethyl 1-(3-cyano-4-(2-ethylbutoxy)phenyl)pyrazole-4-carboxylate, melting point 114–115°C.

EXAMPLE 14

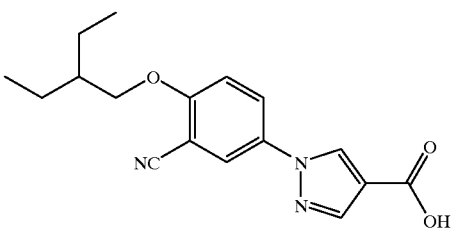

To a solution (10 ml) of ethyl 1-(3-cyano-4-(2-ethylbutoxy)phenyl)pyrazole-4-carboxylate (0.88 g) in ethanol was added 2 N aqueous sodium hydroxide solution (1.5 ml) with siring and the mixture was heated at 70° C. for 1 hour. After the completion of the reaction, the reaction mixture was poured into water and neutralized with acetic acid. The precipitated crystals were recrystallized from ethyl acetate to give 0.21 g of 1-(3-cyano-4-(2-ethylbutoxy)phenyl)pyrazole-4-carboxylic acid, melting point 180–182° C.

EXAMPLE 15

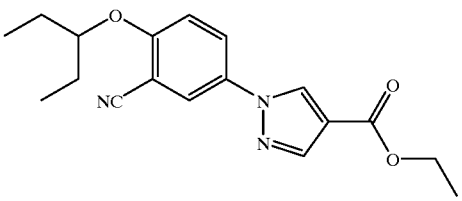

To a solution (15 ml) of ethyl 1-(3-cyano-4-hydroxyphenyl)pyrazole-4-carboxylate (1 g ) obtained in Starting Material Synthetic Example 4 in dimethylformamide were added potassium carbonate (1.2 g) and 3-bromopentane (1.15 g) with stirring, and the mixture was heated at 90° C. for 2 hours. After the completion of the reaction, the reaction mixture was poured into water and the mixture was extracted with toluene, washed with water and dried over magnesium sulfate. The solvent was evaporated under reduced pressure, and the obtained residue was recrystallized from isopropyl ether to give 0.8 g of ethyl 1-(3-cyano-4-(2-ethylpropoxy)phenyl)pyrazole-4-carboxylate, melting point 104° C.

EXAMPLE 16

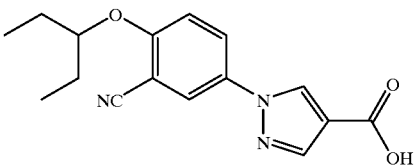

To a solution (10 ml) of ethyl 1-(3-cyano-4-(1-ethylpropoxy)phenyl)pyrazole-4-carboxylate (0.8 g) in ethanol was added 2 N aqueous sodium hydroxide solution (1.5 ml) with stirring, and the mixture was heated at 80° C. for 30 minutes. After the completion of the reaction, the reaction mixture was poured into water and neutralized with acetic acid. The precipitated crystals were recrystallized from a mixed solvent of ethyl alcohol and water to give 0.6 g of 1-(3-cyano-4-(1-ethylpropoxy)phenyl)pyrazole-4-carboxylic acid, melting point 142–144° C.

EXAMPLE 17

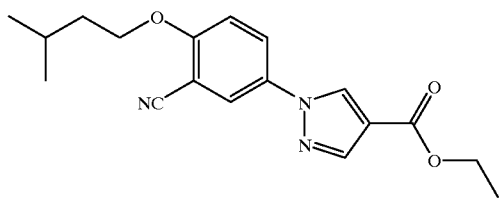

To a solution (15 ml) of ethyl 1-(3-cyano-4-hydroxyphenyl)pyrazole-4-carboxylate (1.5 g) obtained in Staring Material Synthetic Example 4 in dimethylformamide were added potassium carbonate (1.2 g) and 1-bromo-3-methylbutane (1.15 g) with stirring, and the mixture was heated at 90° C. for 1 hour. After the completion of the reaction, the reaction mixture was poured into water and the precipitated crystals were collected by filtration. Recrystallization from ethyl alcohol gave 1.6 g of ethyl 1-(3-cyano-4-(3-methylbutoxy)phenyl)pyrazole-4-carboxylate, melting point 125–126° C.

EXAMPLE 18

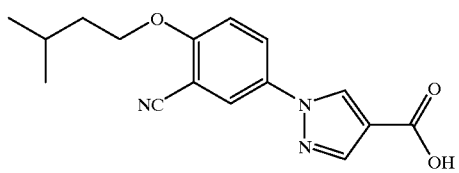

To a solution (15 ml) of ethyl 1-(3-cyano-4-(3-methylbutoxy)phenyl)pyrazole-4-carboxylate (1.6 g) in ethanol was added 1.5 N aqueous sodium hydroxide solution (4 ml) with stirring, and the mixture was heated at 80° C. for 30 minutes. After the completion of the reaction, the reaction mixture was poured into water and neutralized with acetic acid. The precipitated crystals were recrystallized from ethyl acetate to give 0.97 g of 1-(3-cyano-4-(3-methylbutoxy)phenyl)pyrazole-4-carboxylic acid, melting point 210–211° C.

EXAMPLE 19

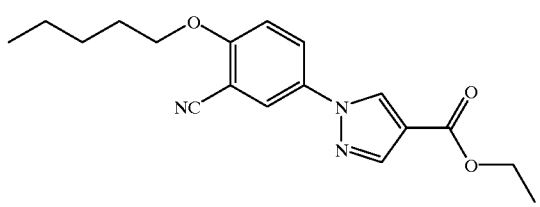

The same reaction and treatment as in Example 5 using ethyl 1-(3-cyano-4-hydroxyphenyl) pyrazole-4-carboxylate obtained in Starting Material Synthetic Example 4 and 1-bromopentane gives ethyl 1-(3-cyano-4-pentyloxyphenyl)-pyrazole-4-carboxylate.

EXAMPLE 20

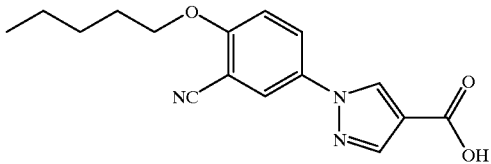

The same reaction and treatment as in Example 6 using ethyl 1-(3-cyano-4-pentyloxyphenyl) pyrazole-4-carboxylate gives ethyl 1-(3-cyano-4-pentyloxy-phenyl) pyrazole-4-carboxylate.

EXAMPLE 21

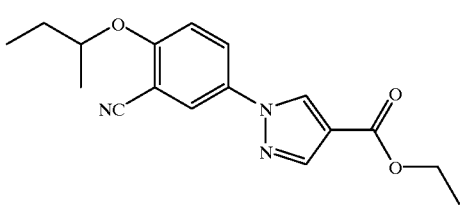

The same reaction and treatment as in Example 5 using ethyl 1-(3-cyano-4-hydroxyphenyl)pyrazole-4-carboxylate and 1-bromo-1-methylpropane gives ethyl 1-(3-cyano-4-sec-butoxyphenyl)pyrazole carboxylate.

EXAMPLE 22

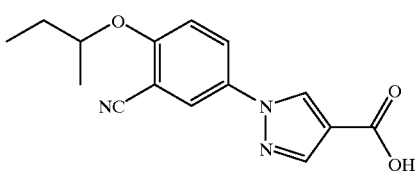

The same reaction and treatment as in Example 6 using ethyl 1-(3cyano-4-sec-butoxyphenyl)pyrazole-4-carboxylate give 1-(3-cyano-4-sec-butoxyphenyl)-pyrazole-4-carboxylic acid.

EXAMPLE 23

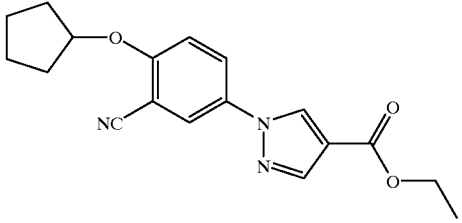

The same reaction and treatment as in Example 5 using ethyl 1-(3-cyano-4-hydroxyphenyl)pyrazole-4-carboxylate and cyclopentyl bromide gives ethyl 1-(3-cyano-4-cyclopentyloxyphenyl)pyrazole carboxylate.

EXAMPLE 24

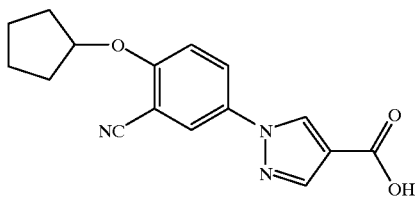

The same reaction and treatment as in Example 6 using ethyl 1-(3-cyano-4-cyclopentyloxyphenyl)pyrazole-4-carboxylate gives 1-(3-cyano-4-cyclopentyl-oxyphenyl) pyrazole-4-carboxylic acid.

EXAMPLE 25

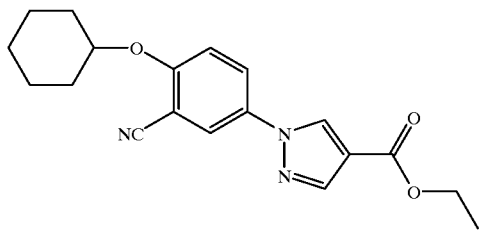

The same reaction and treatment as in Example 5 using ethyl 1-(3-cyano-4-hydroxyphenyl)pyrazole-4-carboxylate and cyclohexyl bromide gives ethyl 1-(3-cyano-4-cyclohexyloxyphenyl)pyrazole-4-carboxylate.

EXAMPLE 26

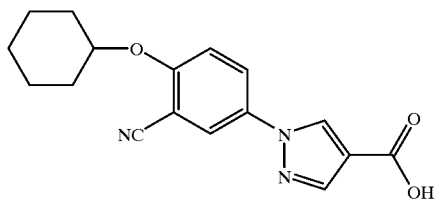

The same reaction and treatment as in Example 6 using ethyl 1-(3-cyano-4-cyclohexyloxyphenyl) pyrazole-4-carboxylic gives 1-(3-cyano-4-cyclohexyloxy-phenyl) pyrazole-4-carboxylic acid.

EXAMPLE 27

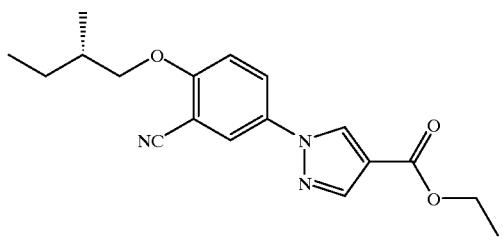

To a solution (10 ml) of ethyl 1-(3-cyano-4-hydroxyphenyl)pyrazole-4-carboxylate (1.5 g) in dimethylformamide were added potassium carbonate (0.91 g) and (S)-(+)-1-bromo-2-methylbutane (1 g) with stirring, and the mixture was heated at 90° C. for 2 hours. After the completion of the reaction, the reaction mixture was poured into water and the mixture was acted with ethyl acetate, washed with water and dried over magnesium sulfate. The solvent was evaporated under reduced pressure and the obtained residue was recrystallized from isopropyl ether to give 1.7 g of ethyl 1-(3-cyano-4-((S)-2-methylbutoxy)phenyl) pyrazole-4-carboxylate, melting point 105–106° C.

EXAMPLE 28

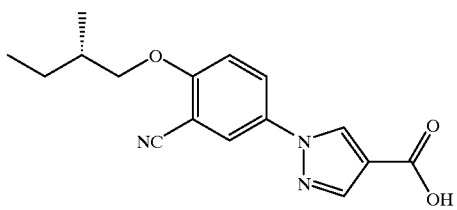

To a solution (10 ml) of ethyl 1-(3-cyano-4-((S)-2-methylbutoxy)phenyl)-pyrazole-4-carboxylate (1.7 g) in ethanol was added 1 N aqueous sodium hydroxide solution (6.3 ml) with stirring, and the mixture was heated at 80° C. for 30 minutes. After the completion of the reaction, the reaction mixture was pouted into water and neutralized with acetic acid. The precipitated crystals were recrystallized from a mixed solvent of ethyl alcohol and water to give 0.8 g of 1-(3-cyano-4-((S)-2-methylbutoxy) phenyl)pyrazole-4-carboxylic acid, melting point 184–186° C. [α] $D_{25}$+10.49° (c=0.5,MeOH)

EXAMPLE 29

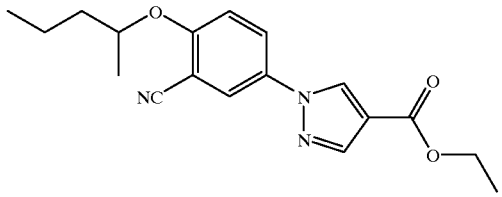

The same reaction and treatment as in Example 5 using ethyl 1-(3-cyano-4-hydroxyphenyl)pyrazole-4-carboxylate gives ethyl 1-(3-cyano-4-(1-methylbutoxy)-phenyl) pyrazole-4-carboxylate.

EXAMPLE 30

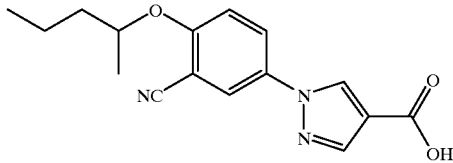

The same reaction and treatment as in Example 6 using ethyl 1-(3-cyano-4-(1-methylbutoxy)phenyl)pyrazole-4-carboxylate gives 1-(3-cyano-4-(1-methylbutoxy)-phenyl) pyrazole-4-carboxylic acid.

EXAMPLE 31

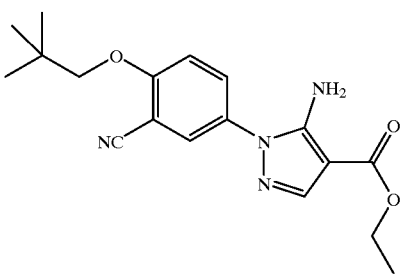

To a solution (100 ml) of 3-cyano-4-neopentyloxyphenylhydrazine (17 g) obtained in Starting Material Synthetic Example 3 in ethanol was added ethyl 2-cyano-3-ethoxyacrylate (14.4 g) with stirring, and the mixture was refluxed under heating for 2 hours. After cooling, the precipitated crystals were collected by filtration to give 18 g of ethyl 5-amino-1-(3-cyano-4-neopentyloxyphenyl)pyrazole-4-carboxylate, melting point 160–162620 C.

EXAMPLE 32

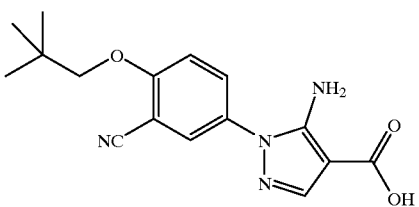

To a solution (17 ml) of ethyl 5-amino-1-(3-cyano-4-neopentyloxyphenyl)pyrazole-4-carboxylate (1.7 g) in ethanol was added 2 N aqueous sodium hydroxide solution (3 ml) with stirring, and the mixture was refluxed under heating for 2 hours. After the completion of the reaction, the reaction mixture was poured into water and neutralized with acetic acid. The precipitated crystals were recrystallized from a mixed solvent of dioxane and water to give 0.64 g of 5-amino-1-(3-cyano-4-neopentyloxyphenyl)pyrazole-4-carboxylic acid, melting point 212° C. (decomposition).

EXAMPLE 33

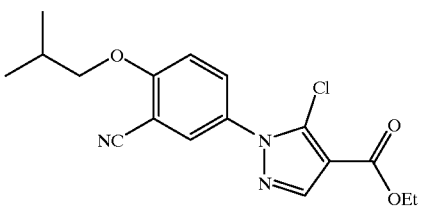

To a solution (15 ml) of ethyl 5-amino-1-(3-cyano-4-isobutoxyphenyl) pyrazole-4-carboxylate (2 g) obtained in Example 1 in con. Hydrochloric acid was added an aqueous solution (4 ml) of sodium nitrite (0.62 g) with stirring under ice-cooling. To this diazonium salt solution was gradually added copper (I) chloride (1.49 g) under ice-cooling. After the dropwise addition, the reaction mixture was heated at 60° C. for 1 hour. After the completion of the reaction, the reaction mixture was ejected with ethyl acetate, washed with water and dried over magnesium sulfate. The solvent was evaporated under reduced pressure and the obtained residue was applied to silica gel column chromatography to give 0.76 g of ethyl 5-chloro-1-(3-cyano-4-isobutoxyphenyl) pyrazole-4-carboxylate, melting point 87° C.

EXAMPLE 34

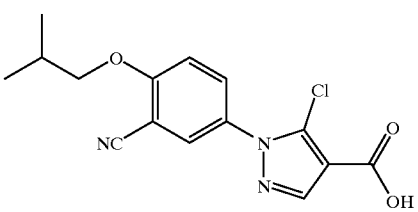

To a solution (10 ml) of ethyl 5-chloro-1-(3-cyano-4-isobutoxyphenyl)-pyrazole-4-carboxylate (1.05 g) in ethanol was added 1 N aqueous sodium hydroxide solution (3.6 ml) with string, and the mixture was heated at 60° C. for 1 hour. After the completion of the reaction, the reaction mixture was pouted into water and neutralized with acetic acid. The precipitated crystals were recrystallized from ethyl acetate to give 0.5 g of 5-chloro-1-(3-cyano-4-isobutoxyphenyl) pyrazole-4-carboxylic acid, melting point 216–218° C.

EXAMPLE 35

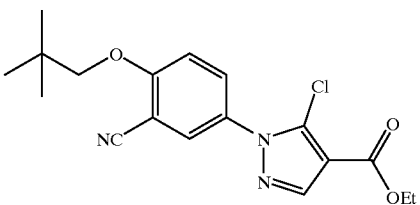

To a solution (15 ml) of ethyl 5-amino-1-(3-cyano-4-neopentyloxyphenyl)pyrazole-4-carboxylate (2.09 g) obtained in Example 31 in con. hydrochloric acid was added an aqueous solution (4 ml) of sodium nitrite (0.62 g) with stirring under ice-cooling. To this diazonium salt solution was gradually added copper (I) chloride (1.49 g) under ice-cooling. After the dropwise addition, the reaction mixture was heated at 60° C. for 1 hour. After the completion of the reaction, the reaction mix was enacted with ethyl acetate, washed with water and dried over magnesium sulfate. The solvent was evaporated under reduced pressure and the obtained residue was applied to silica gel column chromatography to give 0.74 g of ethyl 5chloro-1-(3-cyano-4-neopentyloxyphenyl)pyrazole-4-carboxylate, melting point 90–92° C.

EXAMPLE 36

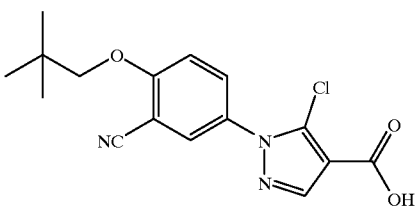

To a solution (10 ml) of ethyl 5-chloro-1-(3-cyano-4-neopentyloxyphenyl)pyrazole-4-carboxylate (1.01 g) in ethanol was added 1 N aqueous sodium hydroxide solution (3.4 ml) with stirring, and the mixture was heated at 60° C. for 1 hour. After the completion of the reaction, the reaction mixture was poured into water and neutralized with acetic acid. The precipitated crystals were recrystallized from ethyl acetate to give 0.46 g of 5-chloro-1-(3-cyano-4-neopentyloxyphenyl)pyrazole-4-carboxylic acid, melting point 212° C.

EXAMPLE 37

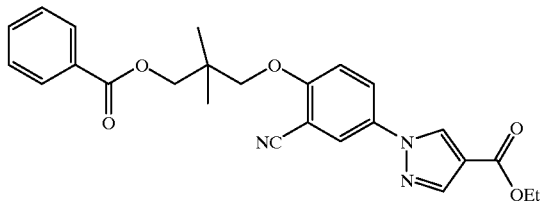

To a solution (25 ml) of ethyl 1-(3-cyano-4-hydroxyphenyl)pyrazole-4-carboxylate (2.6 g) obtained in Staring Material Synthetic Example 4 in dimethylformamide were added potassium carbonate (1.66 g) and 2,2-dimethyl 3-iodidepropyl benzoate (1 g) with stirring, and the mixrture was refluxed under heating at 90° C. for 2 hours. After the completion of the reaction, the reaction mixture was poured into water and the mixture was extracted with ethyl acetate, washed with water and dried over magnesium sulfate. The solvent was evaporated under reduced pressure and the obtained residue was applied to silica gel column chromatography to give 2.89 g of ethyl 1-(4-(3-benzoyloxy-2,2-di methylpropoxy)-3-cyanophenyl)pyrazole-4-carboxylate, melting point 112–114° C.

EXAMPLE 38

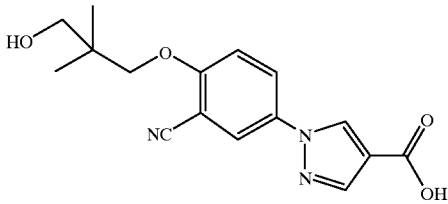

To a solution (20 ml) of ethyl 1-(4-(3-benzoyloxy-2,2-di methylpropoxy)-3-cyanophenyl) pyrazole-4-carboxylate (2.89 g) obtained in Example 37 in ethanol was added 1 N aqueous sodium hydroxide solution (14.2 ml) with stirring, and the mixture was heated at 50° C. for 3 hours. After the completion of the reaction, the reaction mixture was poured into water and neutralized with 1 N hydrochloric acid (15 ml). The precipitated crystals were recrystallized from ethyl acetate to give 0.3 g of 1-(3-cyano-4-(2,2-dimethyl 3-hydroxypropoxy)phenyl)pyrazole-4-carboxylic acid, melting point 188–190° C.

EXAMPLE 39

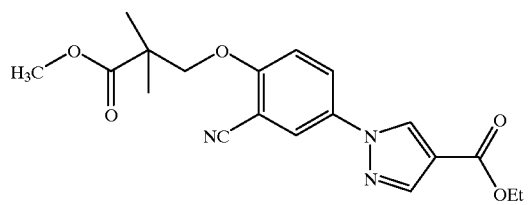

To a solution (10 ml) of ethyl 1-(3-cyano-4-hydroxyphenyl)pyrazole-4-carboxylate (1.0 g) obtained in Starting Material Synthetic Example 4 in dimethylformamide were added potassium carbonate (0.81 g) and methyl 2,2-dimethyl 3-iodidepropionate (1.9 g) with stirring, and the mixture was refluxed under heating at 130° C. for 1 hour. After the completion of the reaction, the reaction mixture was poured into water and the mixture was extracted with ethyl acetate, washed with water and dried over magnesium sulfate. The solvent was evaporated under reduced pressure and the obtained residue was applied to silica gel column chromatography to give 0.64 g of ethyl 1-(3-cyano-4-(2-methyl 2-methoxycarbonylpropoxy) phenyl)pyrazole-4-carboxylate, melting point 95–96° C.

EXAMPLE 40

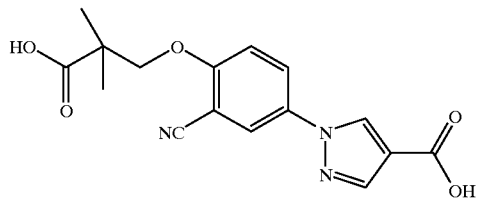

To a solution (6.4 ml) of ethyl 1-(3-cyano-4-(2-methyl-2-methoxy-carbonylpropoxy)phenyl)pyrazole-4-carboxylate (0.64 g) obtained in Example 39 in ethanol was added 2 N aqueous sodium hydroxide solution (2.15 ml) with stirring, and the mixture was heated at 50° C. for 8 hours. After the completion of the reaction, the reaction mxture was poured into water and neutralized with 1 N hydrochloric acid (3.8 ml). The precipitated crystals were recrystallized from a mixed solvent of ethyl alcohol and water to give 0.26 g of 1-(4-(2-carboxy 2-methylpropoxy)-3cyanophenyl)pyrazole-4-carboxylic acid, melting point 230–233° C.

EXAMPLE 41

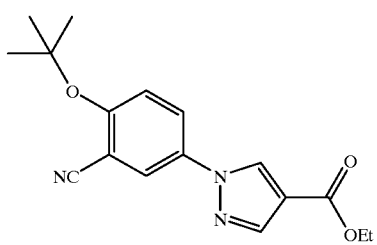

The same reaction and treatment as in Example 5 using ethyl 1-(3cyano-4-hydroxyphenyl)pyrazole-4-carboxylate and 1-bromo-1,1-dimethylethane gives ethyl 1-(4-tert-butoxy-3-cyanophenyl)pyrazole-4-carboxylate.

EXAMPLE 42

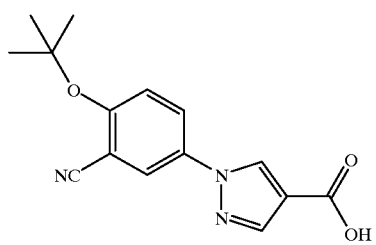

The same reaction and treatment as in Example 6 using ethyl 1-(4tert-butoxy-3-cyanophenyl)pyrazole-4-carboxylate gives 1-(4tert-butoxy-3-cyanophenyl) pyrazole-4-carboxylic acid.

FORMULATION EXAMPLE 1

The compound (50 mg) of the present invention was thoroughly admixed with lactose (98 mg), corn starch (45 mg) and hydroxypropylcellulose (3 mg) in a kneader. The kneaded product was passed through a 200 mesh sieve, dried at 50° C. and passed through a 24 mesh sieve. The resulting product was mixed with talc (3 mg) and magnesium stearate (1 mg) and prepared into tablets weighing 200 mg using a 9 mm diameter pounder. The tablets may be sugar-coated or film coated as necessary.

The superior pharmacological activity of the compound of formula (1) can be demonstrated by the following series of tests.

EXPERIMENTAL EXAMPLE 1

Inhibitory Activity Against Xanthine Oxidase

To 0.136 M Tris-HCl buffer (pH 8.1, 0.95 ml) were added a sample solution (0.15 ml) and a xanthine oxidase solution (0.10 ml), and then a xanthine solution (0.3 ml) to give an enzyme reaction solution. The enzyme reaction solution was incubated at 37° C. At 30 minutes after the initiation of incubation, 20% aqueous trichloroacetic acid solution (1.5 ml) was added to stop the reaction. This solution was transferred to a quartz cell and absorbance at 290 nm was measured by spectrophotometer (Japan Spectroscopic Co., LTD.) Using the obtained measure, xanthine oxidase inhibition percentage was calculated from the following formula, from which $IC_{50}$ of xanthine oxidase inhibitor activity was determined.

Inhibiton (%)=(1−absorbance with sample/absorbance without sample)×100

As a result, the $IC_{50}$ of allopurinol was 300 nM and that of the compound of the present invention was not more than 30 nM, thus demonstrating a strong inhibitory activity.

EXPERIMENTAL EXAMPLE 2

Lowering of Uric Acid Value of Mouse Serum

A sample suspended in 0.5% aqueous hydroxypropyl methyl cellulose (HPMC) solution was forcibly administered into the stomach of 4 to 6 week-old male ICR mice (4 per group) in a dose of 0.3 mg/kg using an oral sound probe. At 2 and 6 hours after the administration of the sample, mice were anesthetized with halothane. Blood samples were taken from both carotid arteries and the mice were exsanguinated. The blood was stood at room temperature for 20–30 minutes and centrifuged at 2000×g for 15 minutes to give serum. The uric acid value was measured using a uric acid measurement kit (manufactured by Wako Pure Chemicals Co.) by phosphotungstic acid method. The obtained values were applied to the following formula to give uric acid value decrease percentage at 2 and 6 hours after the administration of the sample.

Uric acid value decrease (%)=(1−average uric acid value of group administered with sample/average uric acid value of group administered with HPMC)×100

As a result, uric acid value decrease (%) at 2 and 6 hours after the administration of allopurinol was 33% and 14%, respectively. In contrast, the compound of the present invention showed strong uric acid value decrease at 2 hours after the administration of not less than 40% and not less than 20% at 6 hours after the administration.

EXPERIMENTAL EXAMPLE 3

Lowering of Uric Acid Value of Serum of Rats Treated With Oxonic Acid

Oxonic acid, which is a uricase inhibitor, was subcutaneously injected to the back of 6 to 8-week-old male SD rats at 1 hour before administration of sample, and 3 and 9 hours after the administration of sample so that a dose of 250 mg/kg could be achieved, whereby uric acid value in blood was increased.

A sample suspended in 0.5% aqueous hydroxypropyl methyl cellulose (HPMC) solution was forcibly administered into the stomach of rats (4 per group) in a dose of 1 mg/kg using an oral sound probe. Blood samples were taken from rat supraorbital vein before administration of sample and at 0, 2, 4, 6 and 12 hours thereafter. The blood was stood at room temperature for 20–30 minutes and centrifuged at 2000×g for 15 minutes to give serum. The uric acid value was measured using a uric acid measurement kit (manufactured by Wako Pure Chemicals Co.) by phosphotungstic acid method. The obtained values were applied to the following formula to give uric acid value decrease percentage at 2, 4, 6 and 12 hours after the administration of the sample.

Uric acid value decrease (%)=(1−average uric acid value of group administered with sample/average uric acid value of group administered with HPMC)×100

As a result, uric acid value decrease (%) at each time by the compound of the present invention was 37%, 36%, 20% and 18% and the compound obviously decreased uric acid value at 12 hours later.

EXPERIMENTAL EXAMPLE 4

Lowering of Uric Acid Value of Serum of New-World Monkeys (Marmosets)

A sample suspended in 0.5% aqueous hydroxypropyl methyl cellulose (HPMC) solution was forcibly administered into the stomach of mature male marmoset in a dose of 10 mg/kg using an oral sound probe. Blood samples were taken from the tail vein at 6 and 24 hours after the administration of sample. The blood was stood at room temperature for 20–30 minutes and centrifuged at 2000×g for 15 minutes to give serum. The uric acid value was measured using a uric acid measurement kit (manufactured by Wako Pure Chemicals Co.) by phosphotungstic acid method. The obtained values were applied to the following formula to give uric acid value decrease percentage at 6 and 24 hours after the administration of the sample.

Uric acid value decrease (%)=(1−average uric acid value of group administered with sample/average uric acid value of group administered with HPMC)×100

As a result, the compound of the present invention decreased uric acid value by not less than 20% even 24 hours after the administration, thus demonstrating sustained lowering action on uric acid value in blood.

EXPEIMENTAL EXAMPLE 5

Inhibitory Effect Against Superoxide Radical Production Due to Xanthine Oxidase

To 50 mM Tris-HCl buffer (pH 7.5) containing 10 $\mu$M lucigenin, 10 $\mu$M xanthine and 0–10 $\mu$M sample is added milk-derived xanthine oxidase in a concentration of 20 mU/ml and chemiluminescence is measured. The inhibitory effect against superoxide radical production of the sample is evaluated by caluculation by the following formula.

Inhibition (%)=(1−cumulative value for 10 minutes of chemiluminescence by addition of sample/cumulative value for 10 minutes of chemiluminescence without addition of sample)×100

EXPERIMENTAL EXAMPLE 6

Inhibitory Effect Against Ischemic Reperfusion Disorder

Male SD rats (7–8 weeks of age, 4–5 rats) are used The sample is orally administered at 60 minutes before renal ischemia in 10, 30 and 100 mg/kg. To the control group and sham operation group are orally administered a solvent of 0.5% aqueous hydroxymethylcellulose solution in 2 ml/kg. Rats are opened under pentobarbital anesthesia, and blood flow of renal artery on both sides is completely stopped with a clamp to produce renal ischemia At 60 minutes after ischemia, the clamp is removed to allow blood flow, and the abdomen is sutured. The rats are allowed free access to food and water. At 24 hours after re-flowing of renal blood, blood is taken from ventral aorta under ether anesthesia and serum is separated. Blood urea nitrogen (BUN) and serum creatinine (CRE) are measured as indices of renal function disorder by an automatic analyzer Hitachi, Ltd.).

The inhibitory effect of sample against renal ischemic reperfusion disorder is evaluated by calculation by the following formula Inhibition of BUN and CRE increase (%)=(1−average value in group administered with sample/average value in control)×100

EXPERIMENTAL EXAMPLE 7

Inhibitory Effect on Leukotriene-$B_4$ ($LTB_4$) Production

RBL-1 cells (1×10$^6$ cells/ml, DAINIPPON PHARMACEUTICAL CO., LTD.) are cultured in a Dulbecco's modified Eagle medium supplemented with 10% fetal serum albumin, and a sample dissolved in dimethylformamide is added in a final concentration of 0–10 $\mu$M. The mixture is incubated at 37° C. for 5 minutes and left standing in ice for 10 minutes. Then, A23187 (Ca-ionophore) is added to a final concentration of 25 nM and the mixture is incubated at 37° C. for 15 minutes. After the incubation, it is stood again in ice for 10 minutes. Then, supernatant is centrifuged at 3000 rpm for 10 minutes and $LTB_4$ released in the supernatant is quantitatively determined by enzyme immunoassay. Suppression of the production of $LTB_4$, which is considered to be one of the factors involved in ischemic reperfusion disorder, is calculated by the following formula and evaluated.

Inhibition of production (%)=(1−$LTB_4$production with addition of sample/$LTB_4$ production without sample)×100

EXPERIMENTAL EXAMPLE 8

Acute Toxicity

The compound of the present invention (300 mg/kg was administered to four mice once and the mice were monitored for 5 days. No death case was observed.

INDUSTRIAL APPLICABILITY

The 1-phenylpyrazole compound, an optical isomer thereof and a pharmaceutically acceptable salt thereof of the present invention are xanthine oxidase inhibitors having selective and strong inhibitory activity against xanthine oxidase, and are useful drugs effective for hyperuricacidemia and gout caused thereby, in view of the strong and sustained lowering action on blood uric acid value as demonstrated by in vivo tests. They are expected to be highly safe therapeutic agents of hyperuricacidemia and gout, which cause less side effects such as hypersensitive symptoms (e.g., anthema, hives and the like) or renal and hepatic disorders, seen when a conventional, hypoxanthine-like therapeutic agent of hyperuricacidemia and gout is administered. In addition, the compound of the present invention is expected to serve well as a therapeutic agent of diseases such as hyperuricacidemia and gout, which shows long-lasting effect by a single administration a day.

The compound of the present invention is used for the treatment and prevention of diseases caused by various disorders associated with the generation of active oxygen in organs and tissues. For example, it can be used for diseases associated with ischemic perfusion disorder in various organs, which is caused by the generation of active oxygen. Specific examples include myocardial infarction, cerebral infarction, pulmonary thrombosis, renal and hepatic ischemic organopathy, and postoperative or post-treatment aggravation of the state associated with transdermal and transcervical coronary arterioplasty, vascular bypassing or organ transplantation, which have high possibility of developing temporal ischemic state.

In addition, the compound of the present invention quickly migrates into blood. However, it is not easily metabolized and shows high bioavailability. The compound of the present invention is stable to light and heat, and has superior physical properties.

The present invention is based on application Nos. 284479/1996, 55786/1997 and 261305/1997 filed in Japan, the contents of which are incorporated hereinto by reference.

What is claimed is:

1. A 1-phenylpyrazole compound of the formula (1)

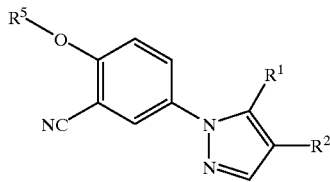

(1)

wherein
- $R^1$ is a hydrogen, a halogen or an amino;
- $R^2$ is a carboxy or a $C_1$–$C_4$ alkoxycarbonyl; and
- $R^5$ is a $C_4$–$C_6$ alkyl, a $C_3$–$C_6$ cycloalkyl or a $C_3$–$C_6$ cycloalkyl-$C_1$–$C_4$ alkyl optionally substituted by 1 or 2 substituents selected from the group consisting of halogen, hydroxy, $C_1$–$C_4$ alkoxy, carboxy, $C_1$–$C_4$ alkoxycarbonyl and acyloxy, an optical isomer thereof or a pharmaceutically acceptable salt thereof.

2. The 1-phenylpyrazole compound of claim 1, wherein $R^5$ is $C_4$–$C_6$ alkyl, $C_3$–$C_6$ cycloalkyl or $C_3$–$C_6$ cycloalkyl-$C_1$–$C_4$ alkyl, an optical isomer thereof or a pharmaceutically acceptable salt thereof.

3. The 1-phenylpyrazole compound of claim 1, which is a member selected from the group consisting of
- 5-amino-1-(3-cyano4-isobutoxyphenyl)pyrazole-4-carboxylic acid,
- ethyl 1-(3-cyano-4-isobutoxyphenyl)pyrazole-4-carboxylate,
- 1-(3-cyano-4-isobutoxyphenyl)pyrazole-4-carboxylic acid,
- 1-(4-butoxy-3-cyanophenyl)pyrazole-4-carboxylic acid,
- 1-(3-cyano-4-cyclopropylmethoxyphenyl)pyrazole-4-carboxylic acid,
- 1-(3-cyano-4-neopentyloxyphenyl)pyrazole-4-carboxylic acid,
- 1-(3-cyano-4-(2-ethylbutoxy)phenyl)pyrazole-4-carboxylic acid,
- 1-(3-cyano-4-(1-ethylpropoxy)phenyl)pyrazole-4-carboxylic acid,
- 1-(3-cyano-4-(3-methylbutoxy)phenyl)pyrazole-4-carboxylic acid,
- 1-(3-cyano-4-((S)-2-methylbutoxy)phenyl)pyrazole-4-carboxylic acid,
- 5-amino-1-(3-cyano-4-neopentyloxyphenyl)pyrazole-4-carboxylic acid, and
- 5-chloro-1-(3-cyano-4-neopentyloxyphenyl)pyrazole-4-carboxylic acid, an optical isomer thereof or a pharmaceutically acceptable salt thereof.

4. A pharmaceutical composition comprising the 1-phenylpyrazole compound of claim 1, an optical isomer thereof or a pharmaceutically acceptable salt thereof, and a pharmaceutically acceptable carrier.

5. A method of inhibiting xanthine oxidase which comprises administering to a patient in need of same a 1-phenylpyrazole compound of claim 1, an optical isomer thereof or a pharmaceutically acceptable salt thereof.

* * * * *